US008133881B2

(12) United States Patent
Mickle et al.

(10) Patent No.: US 8,133,881 B2
(45) Date of Patent: *Mar. 13, 2012

(54) CARBOHYDRATE CONJUGATES TO PREVENT ABUSE OF CONTROLLED SUBSTANCES

(75) Inventors: Travis Mickle, Coralville, IA (US); Thomas Piccariello, Blacksburg, VA (US); James Scott Moncrief, Christiansburg, VA (US); Nancy Johnston Boerth, Blacksburg, VA (US); Barney Bishop, Annandale, VA (US)

(73) Assignee: Shire LLC, Florence, KY (US)

( * ) Notice: Subject to any disclaimer, the term of this patent is extended or adjusted under 35 U.S.C. 154(b) by 702 days.

This patent is subject to a terminal disclaimer.

(21) Appl. No.: 11/179,801

(22) Filed: Jul. 13, 2005
(Under 37 CFR 1.47)

(65) Prior Publication Data
US 2007/0197451 A1    Aug. 23, 2007

Related U.S. Application Data

(63) Continuation-in-part of application No. PCT/US2004/000646, filed on Jan. 13, 2004, and a continuation-in-part of application No. 10/923,257, filed as application No. PCT/US03/05525 on Feb. 24, 2003, now Pat. No. 7,622,441, and a continuation-in-part of application No. 10/923,088, filed on Aug. 23, 2004.

(60) Provisional application No. 60/439,468, filed on Jan. 13, 2003.

(51) Int. Cl.
*A61K 31/70* (2006.01)
*A61K 31/00* (2006.01)
*A61K 38/00* (2006.01)
*A01N 43/04* (2006.01)
*C12P 19/00* (2006.01)

(52) U.S. Cl. ............ 514/54; 435/72; 424/78.13; 514/1.1
(58) Field of Classification Search .................. None
See application file for complete search history.

(56) References Cited

U.S. PATENT DOCUMENTS

| | | |
|---|---|---|
| 3,843,696 A | 10/1974 | Wagner et al. |
| 3,878,187 A | 4/1975 | Schneider et al. |
| 4,025,501 A | 5/1977 | Leute |
| 4,346,166 A | 8/1982 | Montag et al. |
| 4,356,166 A | 10/1982 | Peterson et al. |
| 4,489,080 A | 12/1984 | Lomen |
| 5,037,883 A | 8/1991 | Kopecek et al. |
| 5,169,933 A | 12/1992 | Anderson et al. |
| 5,183,883 A | 2/1993 | Tanaka et al. |
| 5,196,406 A | 3/1993 | Kamei et al. |
| 5,451,410 A | 9/1995 | Milstein et al. |
| 5,463,022 A | 10/1995 | Inoue et al. |
| 5,643,957 A | 7/1997 | Leone-Bay et al. |
| 5,681,811 A | 10/1997 | Ekwuribe |
| 5,700,459 A | 12/1997 | Krone et al. |
| 5,756,291 A | 5/1998 | Griffin et al. |
| 5,792,451 A | 8/1998 | Sarubbi et al. |
| 5,843,634 A | 12/1998 | Brate et al. |
| 5,851,536 A | 12/1998 | Yager et al. |
| 5,898,033 A | 4/1999 | Swadesh et al. |
| 5,935,995 A | 8/1999 | Bosslet et al. |
| 5,981,507 A | 11/1999 | Josephson et al. |
| 6,005,004 A | 12/1999 | Katz et al. |
| 6,048,736 A | 4/2000 | Kosak |
| 6,074,659 A | 6/2000 | Kunz et al. |
| 6,075,120 A | 6/2000 | Cheronis et al. |
| 6,093,391 A | 7/2000 | Kabanov et al. |
| 6,146,658 A | 11/2000 | Bosslet et al. |
| 6,306,993 B1 | 10/2001 | Rothbard et al. |
| 6,309,633 B1 | 10/2001 | Ekwuribe et al. |
| 6,713,452 B2 | 3/2004 | Ekwuribe et al. |
| 6,716,452 B1 | 4/2004 | Piccariello et al. |
| 6,740,641 B2 | 5/2004 | Gao et al. |
| 6,846,831 B2 | 1/2005 | Clemens |
| 7,060,708 B2 | 6/2006 | Piccariello et al. |
| 7,163,918 B2 | 1/2007 | Piccariello |
| 7,169,752 B2 | 1/2007 | Mickle |
| 7,338,939 B2 | 3/2008 | Mickle |
| 7,375,082 B2 | 5/2008 | Mickle |
| 7,375,083 B2 | 5/2008 | Mickle |
| 7,427,600 B2 | 9/2008 | Mickle |
| 7,438,900 B2 * | 10/2008 | Piccariello et al. ........ 424/78.13 |
| 7,622,441 B2 | 11/2009 | Mickle |
| 2002/0059013 A1 | 5/2002 | Rajala et al. |
| 2002/0099013 A1 | 7/2002 | Piccariello et al. |
| 2003/0091593 A1 | 5/2003 | Bachmann |
| 2003/0130205 A1 | 7/2003 | Christian |
| 2004/0052731 A1 | 3/2004 | Hirsh et al. |
| 2004/0058946 A1 | 3/2004 | Buchwald et al. |
| 2004/0127397 A1 | 7/2004 | Piccariello |

(Continued)

FOREIGN PATENT DOCUMENTS

WO    WO9710829    3/1997

(Continued)

OTHER PUBLICATIONS

U.S. Appl. No. 10/923,088, Entitled "Active Agent Delivery Systems and Methods for Protecting and Administering Active Agents", Mickle et al., filed Aug. 23, 2004.

(Continued)

*Primary Examiner* — Maury Audet
(74) *Attorney, Agent, or Firm* — McDermott Will & Emery LLP

(57) ABSTRACT

The invention provides a "street-safe" version of a controlled substance that permits the therapeutically beneficial effects of the substance while reducing or eliminating the euphoric effects that lead to substance abuse. The invention provides pharmaceutical compositions comprising a controlled substance and a carbohydrate covalently bound to said controlled substance in a manner that renders said controlled substance pharmacologically inactive or substantially diminishes its activity and methods of using the same.

3 Claims, 5 Drawing Sheets

U.S. PATENT DOCUMENTS

| | | |
|---|---|---|
| 2004/0161382 A1 | 8/2004 | Yum et al. |
| 2005/0038121 A1 | 2/2005 | Mickle et al. |
| 2005/0054561 A1 | 3/2005 | Mickle et al. |
| 2005/0065086 A1 | 3/2005 | Kirk et al. |
| 2005/0069550 A1 | 3/2005 | Mickle et al. |
| 2005/0074425 A1 | 4/2005 | Waugh et al. |
| 2005/0080012 A1 | 4/2005 | Mickle et al. |
| 2005/0112088 A1 | 5/2005 | Zhao et al. |
| 2005/0176644 A1 | 8/2005 | Mickle et al. |
| 2005/0176645 A1 | 8/2005 | Mickle et al. |
| 2005/0176646 A1 | 8/2005 | Mickle et al. |
| 2005/0266070 A1 | 12/2005 | Mickle et al. |
| 2006/0014697 A1 | 1/2006 | Mickle et al. |
| 2007/0060500 A1 | 3/2007 | Mickle |
| 2007/0066537 A1 | 3/2007 | Mickle |
| 2007/0203055 A1 | 8/2007 | Mickle |
| 2008/0090771 A1 | 4/2008 | Moncrief |
| 2008/0207668 A1 | 8/2008 | Moncrief |
| 2009/0036553 A1 | 2/2009 | Piccariello |
| 2009/0253792 A1 | 10/2009 | Mickle |
| 2009/0306228 A1 | 12/2009 | Mickle |
| 2010/0105781 A1 | 4/2010 | Mickle |
| 2010/0144645 A1 | 6/2010 | Kirk |
| 2011/0009669 A1 | 1/2011 | Mickle |
| 2011/0040072 A1 | 2/2011 | Mickle |
| 2011/0046226 A1 | 2/2011 | Mickle |

FOREIGN PATENT DOCUMENTS

| | | |
|---|---|---|
| WO | WO9812228 | 3/1998 |
| WO | WO9843677 | 10/1998 |
| WO | WO 01-79244 | 10/2001 |
| WO | WO-0224715 | 3/2002 |
| WO | WO-02094173 | 11/2002 |
| WO | WO 02-098451 | 12/2002 |
| WO | WO-03057716 | 7/2003 |
| WO | WO-03072046 | 9/2003 |

OTHER PUBLICATIONS

U.S. Appl. No. 10/953,111, Entitled "Compounds and Compositions for the Prevention of Overdose of Oxycodone", Mickle et al., filed Aug. 23, 2004.

U.S. Appl. No. 11/392,878, Entitled "Pharmaceutical Compositions for Prevention of Overdose or Abuse", Mickle et al., filed Apr. 4, 2006.

U.S. Appl. No. 11/400,304, Entitled "Abuse Resistant Amphetamine Prodrugs", Mickle et al., filed Apr. 10, 2006.

International Search Report of Aug. 9, 2006.

Japan Office Action dated May 12, 2010 for Japanese Patent Application No. 2006-500902 (English translation thereof), corresponding to the instant application U.S. Appl. No. 11/179,801.

Okada, Masahiko, et al., "Synthesis of Glycopeptide-conjugates via Ring-Opening Polymerization of Sugar-Substituted .alpha.-Amino Acid N-Carboxyanhydrides (GlycoNCAs)," Proc. Japan Acad., 73:205-209 (1997).

International Search Report dated Sep. 16, 2003, for PCT/US2003/000379.

International Search Report dated Oct. 9, 2003, for PCT/US2003/005525.

International Search Report dated Jan. 25, 2005, for PCT/US2004/000646.

Casparis, et al., "Alkaloid glycosides. IV Codeine", Pharmaceutica Acta Helvetiae (1949), 24, 145-55.

* cited by examiner

CARBOHYDRATE CONJUGATES TO PREVENT ABUSE OF CONTROLLED SUBSTANCES

CROSS REFERENCE RELATED APPLICATIONS

This application is a continuation-in-part application and claims benefit under 35 U.S.C. §120 of PCT/US04/00646 filed Jan. 13, 2004, which claims benefit under 35 U.S.C. §119(e) of U.S. Provisional application 60/439,468 filed Jan. 13, 2003; and is a continuation-in-part application of U.S. application Ser. No. 10/923,257 filed Aug. 23, 2004 now U.S. Pat. No. 7,622,441; which claims the benefit of PCT/US03/05525 filed Feb. 24, 2003; and is a continuation-in-part application of U.S. application Ser. No. 10/923,088 filed Aug. 23, 2004, each of which are hereby incorporated by reference in their entirety.

BACKGROUND OF THE INVENTION (i) Field of the Invention

The invention relates to novel pharmaceutical compounds and more particularly to controlled substances that are covalently bound to a chemical moiety and thus rendered pharmaceutically inactive until broken down by enzymatic and/or chemical means in a time-dependent manner following oral administration. Delayed release from the conjugate prevents spiking of drug levels and affords gradual release over an extended period of time. The enzymatic and/or chemical conditions necessary for the release of the controlled substance are either not present or of minimal activity when the novel pharmaceutical compound is introduced nasally, inhaled, or injected; thus, also preventing spiking when administered by these routes. Controlled substances with these novel properties are less likely to be abused due to the diminished "rush" effect of the modified controlled substance. Consequently, the therapeutic value of these pharmaceuticals is enhanced by decreasing euphoria while increasing the duration of the analgesic effect.

(ii) Description of the Related Art

A number of pharmacologically useful compounds are also commonly abused controlled substances. In particular, analgesics that are prescribed for the management of acute and chronic pain have become increasingly abused over the last decades. For example, the increase in prescription of oxycodone in the last few years led to widespread abuse of this drug in certain areas of the U.S. Amphetamines are another example of controlled substances with important pharmacological uses that also are highly addictive and commonly abused. There has been considerable effort in research to develop new compounds with the pharmacological benefits of these drugs, but that are less addictive or less likely to be abused.

The need for "street safe" narcotics was highlighted recently by the epidemic of problems associated with the long-acting analgesic OxyContin, an extended release form of oxycodone. Numerous media reports described the rapidly growing frequency of abuse of this potent narcotic which contains high levels of oxycodone formulated into an extended release matrix. The problem was summarized recently in the following extract from a web page of the National Institute for Drug Abuse (NIDA):

A variety of sources, including NIDA's own Community Epidemiology Work Group, a network of epidemiologists and researchers from 21 major U.S. metropolitan areas who monitor and report on community-level trends in drug abuse, are finding that people are "short circuiting" the time-release form of this medication by chewing, crushing, or dissolving the pills. Chewing or crushing the prescription drug corrupts or foils its time-release protection, enabling the users to experience a rapid and intense euphoria that does not occur when taken as designed and prescribed. Once having crushed the pills, the individuals are injecting, inhaling, or taking them orally, often with other pills, marijuana, or alcohol. Although the injecting and "snorting" routes of administration are most associated with drug abuse "a Drug Enforcement Administration (DEA) study found that the vast majority of 110 people identified in the previous two years as having overdosed on OxyContin took the drug orally as opposed to snorting or injecting a crushed tablet (see *ADAW*, Nov. 19, 2001). Rapid release of the medication in people who are not tolerant can be fatal."

SUMMARY OF THE INVENTION

The invention provides a "street-safe" version of a controlled substance which permits the therapeutically beneficial effects of the substance while reducing or eliminating the euphoric effects that lead to substance abuse. An embodiment of the invention provides a controlled substance that has been chemically modified to released the controlled substance only under selected conditions which do not give rise to or reduce the euphoric effect. A further aspect of the invention permits the release to occur at a controlled rate that does not give rise to or reduces the euphoric effect.

Another embodiment provides a chemically modified controlled release substance that is inactive and resistant to absorption until broken down by chemical or enzymatic means at the desired target location, such as under the acidic conditions of the stomach and/or the enzymatic activity present in the gastrointestinal tract. In a preferred embodiment, the breakdown does not occur until the conjugate has passed into the colon.

One embodiment of the invention provides a composition which resistant to oral abuse through the covalent modification of the substance until it is available for absorption.

In another embodiment of the invention, the chemically modified controlled release substance is released in the colon and or bloodstream, at controlled rate that reduces or does not give rise to a euphoric effect.

In one embodiment, the invention comprises a controlled substance that has been rendered inactive or substantially inactive wherein said controlled substance is covalently bonded to the chemical moiety. In a preferred embodiment the chemical moiety is a carbohydrate, more preferably a carbohydrate chain. The carbohydrate chain preferably comprises between 2 and 50 carbohydrate groups, more preferably the carbohydrate chain is between 2 and 10 carbohydrate groups. Most preferably the carbohydrate is between 2 and 5 carbohydrate groups. In another embodiment the carbohydrate is attached to a peptide and the controlled substance is attached to either the carbohydrate or the peptide.

In another embodiment, the invention comprises a controlled substance that has been rendered inactive or substantially inactive wherein the controlled substance is covalently bonded to a carbohydrate which breaks down under the conditions of the colon thereby providing protection for the active agent (substance) through the stomach.

In an oral composition of the invention, absorption of the controlled substance into the bloodstream occurs in a sustained release manner wherein peak concentrations of the drug are decreased when compared to non-conjugated drug given in a similar dosage and formulation.

Another aspect of the invention relates to a method for delivering a controlled substance to a patient so as to obtain a therapeutic, but not a substantial euphoric effect, comprising orally administering a composition of the invention to a patient.

The invention provides a method for delivering a controlled substance to a patient to obtain a therapeutic effect without a substantial euphoric effect, comprising parenterally administering the above composition to the patient.

DETAILED DESCRIPTION OF PREFERRED EMBODIMENTS

Figure 1:
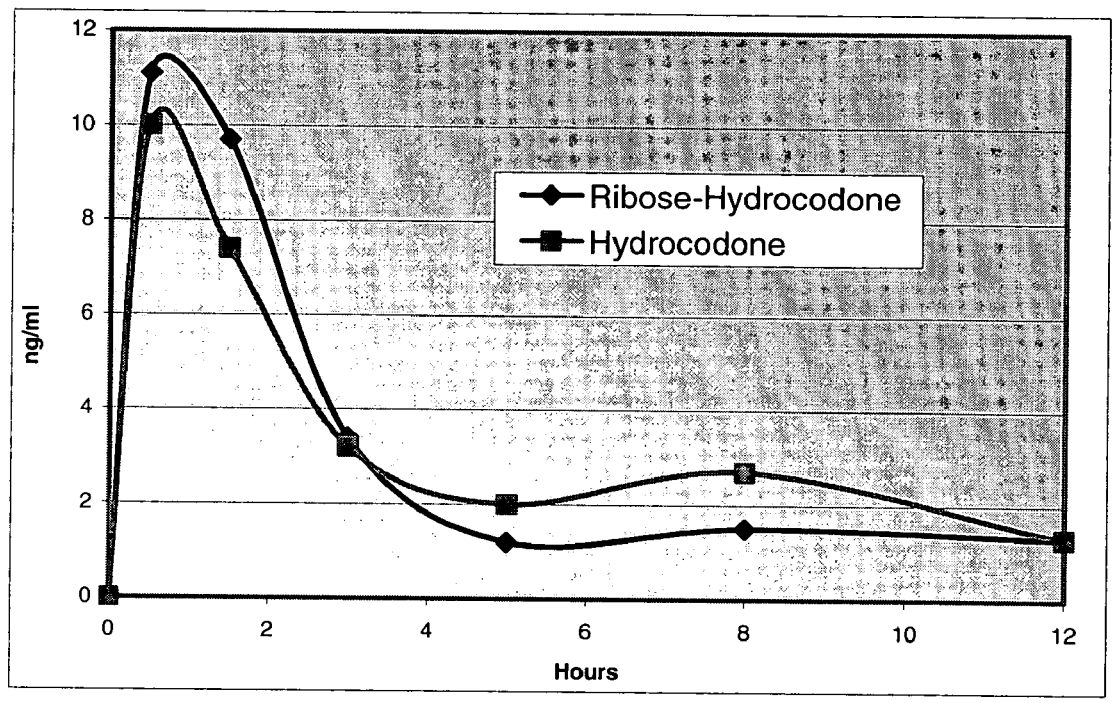
FIG. 1. illustrates mean hydrocodone serum levels compared to a ribose-hydrocodone conjugate orally delivered.

The invention provides methods for altering controlled substances in a manner that decreases their potential for abuse. The novel compositions may be combined in tablets with suitable excipients or formulated in solution for oral delivery. When delivered by the oral route the controlled substance is released in a time-dependent manner (sustained release) by acid hydrolysis and/or enzymatic cleavage. When administered by injection the controlled substance is released in a time-dependent manner (sustained release) by way of serum enzymes.

Terms Defined

Controlled substance—a substance subject to federal regulation of its manufacture, sale, or distribution because of the potential for, or evidence of, abuse; its potential for psychic or physiological dependence; it constitutes a public health risk; scientific evidence of its pharmacologic effect; or its role as a precursor of other controlled substances.

Chemical moiety—a substance made up of chemical elements and characterized by a defined molecular composition. It can exist as a part of the drug conjugate and can be separated from the conjugate. Examples include a carbohydrate or chain of carbohydrates, an amino acid, an oligopeptide, or a polypeptide, but may be any number of other substances.

Although the discussion which follows focuses on oral administration of the controlled substance, it will be appreciated that the compositions and methods of the invention are likewise applicable to other forms of administration, for example, injectable administration of the controlled substance.

Covalent attachment of a chemical moiety to a controlled substance renders the substance pharmacologically inactive and resistant to absorption. Removal of the chemical moiety by enzymatic or chemical means, however, restores the activity and the ability to be absorbed. The conditions of the colon, stomach and/or the enzymatic activity present in the targeted portion of the gastrointestinal tract can therefore affect release of the active controlled substance.

When abused, controlled substances are typically delivered by means other than the oral route, namely by: i) parenteral injection; ii) intranasal delivery; or iii) inhalation. Administration by these routes results in rapid absorption into the bloodstream and the subsequent "rush" effect sought by the user or addict. By contrast, when given by these routes, the covalently modified compound of the invention (adopted for breakdown in the stomach or intestinal tract) is: i) not exposed to the necessary chemical and/or enzymatic conditions for release of the active agent; or ii) the required activity is not present in sufficient amounts to affect rapid release/absorption. The covalently modified controlled substance, therefore, does not produce the euphoric effect sought by users or addicts, but remains effective as a therapeutic.

The invention may be comprised of any controlled substance covalently attached to any chemical moiety, such as narcotics. Preferably, the controlled substance is an analgesic or stimulant. Further, the controlled substance is preferably selected from the following analgesics: codeine, fentanyl, hydrocodone, hydromorphone, levorphanol, methadone, morphine, oxycodone, propoxyphene, and sufentanyl. The controlled substance may also be amphetamine or methylphenidate.

The chemical moiety comprising the invention may be any chemical substance that can be attached to the controlled substance in a manner that renders it pharmacologically inactive. Analgesics and stimulants produce their pharmacological effects through binding to specific receptors or uptake proteins. The attachment of certain chemical moieties can therefore prevent the active substance from binding to receptor(s) or a recognition site on an uptake protein. Further, without wishing to be bound to the theory, the covalent modification is believed to prevent the pharmacological effect by preventing the drug from crossing the blood-brain barrier. Preferably, the attachment of the chemical moiety to the controlled substance will also prevent or substantially delay the absorption of the compound, particularly when the compound is delivered by routes other than oral administration.

Preferably, the attached chemical moiety is a carbohydrate. The carbohydrate chain preferably comprises less than 100 groups, more preferably less than 50 groups and still more preferably less than 10 groups. The carbohydrate is also preferably a sugar.

The attached chemical moiety may be comprised of other naturally occurring or synthetic substances. Controlled substances, for example, could also be attached to lipids, amino acids, polypeptide, nucleic acids, or vitamins. These chemical moieties could be expected to serve the same functions as a carbohydrate; namely, effect delayed release in the gastrointestinal tract and prevent rapid absorption of the active agent.

In one embodiment, the covalently attached chemical moiety is removed by enzymatic activity encountered by the compound in the stomach and/or intestinal tract. The stomach and intestinal tract are bathed in degradative enzymes. For example, the pancreas releases into the small intestine a myriad of hydrolytic enzymes such as glycosidases, proteases, lipases, and amylases, and nucleases. Additionally, the intestinal epithelial cells that line the surface of the GI tract produce various surface associated and intracellular degradative enzymes (e.g. brush border peptidases, esterases). These enzymes degrade proteins, lipids, carbohydrates, and nucleic acids contained in ingested food. Thus, it can be expected that the controlled substance will be released from the attached chemical moiety when the appropriate enzyme(s) is encountered in the gastrointestinal tract.

In another embodiment, the chemical moiety is attached to the controlled substance in a manner in which it is not readily released by conditions found in the mouth (saliva), the intranasal cavity, the surface of the lungs, or in the serum. Extreme acid conditions encountered in the stomach are not present elsewhere in humans. Therefore, any acid dependent release mechanism will occur only after oral administration. Although, degradative enzymes are present in the aforementioned environments, they are not generally present in the high concentrations found in the intestinal tract. Thus, release of the controlled substance by enzymatic cleavage will not occur rapidly when the novel compounds are administered by routes other than oral delivery.

In a specific embodiment of the invention, the analgesic (e.g. oxycodone or hydrocodone) is attached to a ribofuranose (or other combinations of ribose or furanose). The resulting ester linkages can be hydrolyzed by glycosidases encountered in the gastrointestinal tract. Glycosidases are not present at high levels in saliva or on the mucosal surfaces of the nasal cavity, lungs, or oral cavity. Thus, controlled substances attached to ribofuranose by this method would not be rapidly released by saliva or when delivered intranasally or by inhalation.

The following examples are given by way of illustration and in no way should be construed as limiting as to the full scope of the invention. Other embodiments and features of the invention will be obvious from the figures and tables.

EXAMPLES

Hydrocodone, an opioid agonist, was chosen as a model compound for testing conjugates for the hypothesis that conjugates of opioid drugs can afford extended release, while also lowering the potential for abuse.

Example 1

Preparation of the Chloroformate of 2,3-O-isopropylidene-1-methoxy-D-ribofuranose

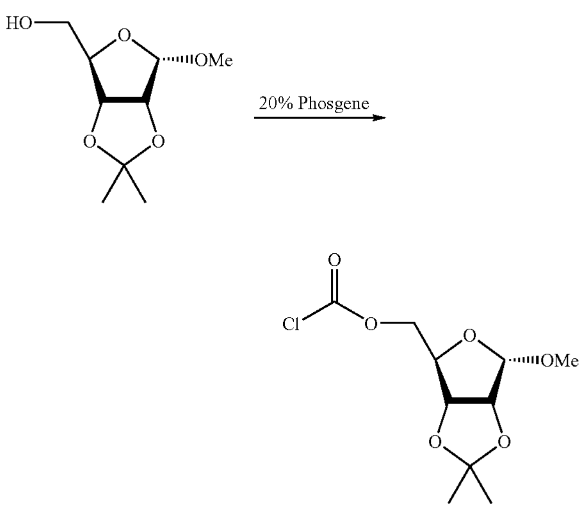

| Reagents | MW | Weight | mmoles | Molar Equivalents |
|---|---|---|---|---|
| 2,3-O-isopropylidene-1-methoxy-D-ribofuranose | 204 | 1.00 g | 3.85 | 1 |
| 20% Phosgene in toluene | — | 25 ml | — | — |

Chloroformate of 2,3-O-isopropylidene-1-methoxy-D-ribofuranose

To a stirring solution of 20% phosgene in toluene under an inert atmosphere was added 2,3-O-isopropylidene-1-methoxy-D-ribofuranose via syringe. The resulting clear, colorless solution was stirred at ambient temperature for 30 minutes. After stirring, Ar(g) was bubbled through the solution for approximately 20 minutes to remove any excess phosgene. Solvent was then removed and product dried under vacuum for 18 hours. Product was used without further purification or characterization.

Example 2

Preparation of Ribo-Hydrocodone

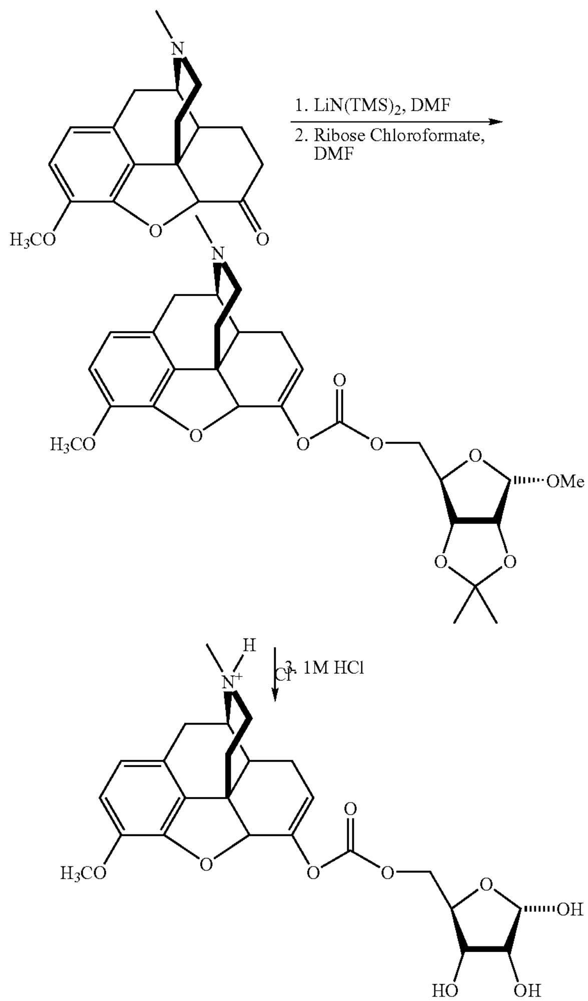

| Reagents | MW | Weight | mmoles | Molar Equivalents |
|---|---|---|---|---|
| 1. Hydrocodone | 299 | 0.733 g | 2.45 | 1.0 |
| 1. LiN(TMS)$_2$ in THF | 1M | 3.68 ml | 3.68 | 1.5 |
| 1. DMF | — | 8 ml | — | — |
| 2. Ribose Chloroformate | — | — | 4.90 | 2.0 |
| 2. DMF | — | 3 ml | — | — |
| 3. 1M HCl | 1M | 10 ml | — | — |

Ribo-Hydrocodone:

To a solution of hydrocodone in DMF was added LiN(TMS)$_2$ in THF via syringe. The solution was stirred at ambient temperatures for 5 minutes then the chloroformate of ribose in DMF was added via syringe. The resulting solution was stirred at ambient temperatures for 2 hours. A TLC was taken (9:1 $CHCl_3$:MeOH; UV and 5% $H_2SO_4$ in MeOH; $R_{f(product)}$=~0.5). Reaction was neutralized to pH 7 with 1M HCl. Solvent was removed. Crude product was taken up in $CHCl_3$ (50 ml), washed with water (3×50 ml), dried over $MgSO_4$, filtered and solvent removed. Final product was purified using preparative HPLC (10 mM $CH_3COONH_4$/MeCN; 0-20 min: 80/20→0/100). Solid was collected as a clear, colorless glass (0.095 g, 7% yield): $^1$H NMR (DMSO-d$_6$), δ 1.26 (s, 3H), 1.39 (s, 3H), 1.50 (m, 2H), 1.89 (s, 4H), 2.08 (m, 2H), 2.29 (s, 4H), 2.40 (m, 2H), 2.88 (d, 1H), 3.08 (m, 1H), 3.25 (s, 3H), 3.73 (s, 3H), 4.12 (m, 2H), 4.28 (t, 1H), 4.58 (d, 1H), 4.72 (d, 1H), 4.97 (s, 1H), 4.98 (s, 1H), 5.70 (s, 1H), 6.66 (d, 1H), 6.75 (d, 1H). MS Calculated mass=529.2. Found=530.4 (M+H).

To the protected ribose intermediate was added 10 ml of 1M HCl. The resulting solution was stirred at ambient temperatures for 2 hours. Solvent was removed and final product dried under vacuum. Solid was collected as a waxy, slightly yellow solid (0.092 g, quant.): $^1$H NMR (DMSO-$d_6$), δ 1.51 (t, 1H), 1.83 (d, 1H), 2.41 (dt, 1H), 2.27 (t, 1H), 2.63 (dd, 1H), 2.80 (s, 3H), 2.96 (m, 2H), 3.20 (m, 1H), 3.75 (s, 3H), 3.82-4.34 (br m, 12H), 5.15 (s, 1H), 5.72 (s, 1H), 6.75 (d, 1H), 6.88 (d, 1H), 11.37 (br s, 1H).

Example 3

Preparation of Galacto-Hydrocodone

Preparation of Galacto-Hydrocodone

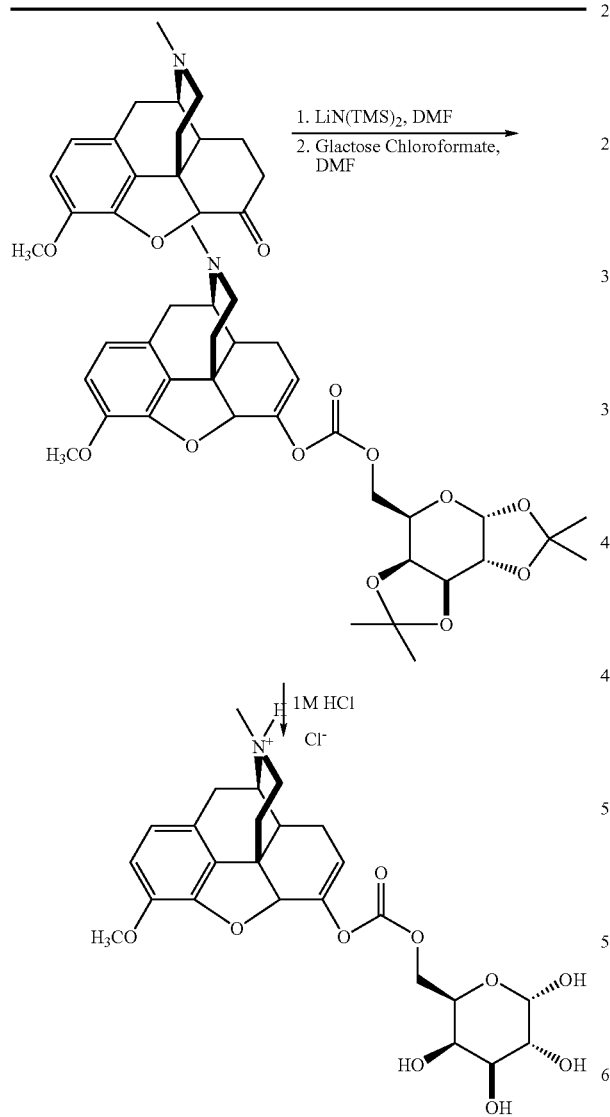

| Reagents | MW | Weight | mmoles | Molar Equivalents |
|---|---|---|---|---|
| 1. Hydrocodone | 299 | 0.223 g | 0.75 | 1.0 |
| 1. LiN(TMS)$_2$ in THF | 1M | 1.13 ml | 1.13 | 1.5 |

-continued

| | | | | |
|---|---|---|---|---|
| 1. DMF | — | 5 ml | — | — |
| 2. Galactose Chloroformate | — | — | 1.49 | 2.0 |
| 2. DMF | — | 3 ml | — | — |
| 3. 1M HCl | 1M | 30 ml | — | — |
| 3. Acetone | — | 20 ml | — | — |

Galacto-Hydrocodone

To a solution of hydrocodone in DMF was added LiN(TMS)$_2$ in THF via syringe. The solution was stirred at ambient temperatures for 5 minutes then the chloroformate of galactose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 6M HCl. Solvent was removed. Final product was purified using preparative TLC (0-10% MeOH in CHCl$_3$). Solid was collected as a white powder (0.180 g, 41% yield): $^1$H NMR (DMSO-$d_6$), δ 1.28 (2s, 6H), 1.37 (s, 3H), 1.44 (3, 3H), 1.49 (m, 2H), 1.88 (dt, 1H), 2.08 (m, 2H), 2.29 (s, 4H), 2.40 (m, 2H), 2.90 (d, 1H), 3.09 (s, 1H), 3.73 (s, 3H), 3.99 (dd, 1H), 4.14 (t, 1H), 4.26 (dt, 2H), 4.39 (d, 1H), 4.63 (d, 1H), 4.95 (s, 1H), 5.48 (d, 1H), 5.68 (d, 1H), 6.65 (d, 1H), 6.74 (d, 1H); MS Calculated mass=585.6. Found=586.4 (M+H).

To the protected galactose intermediate was added 30 ml of 1M HCl and 20 ml acetone. The resulting solution was stirred at ambient temperatures for 3 hours. Solvent was removed and final product dried under vacuum. Solid was collected as a white solid: MS Calculated mass=505.5. Found=506.4 (M+H).

Example 4

Preparation of the Chloroformate of 1,2:3,4-di-O-isopropylidene-D-galactopyranose

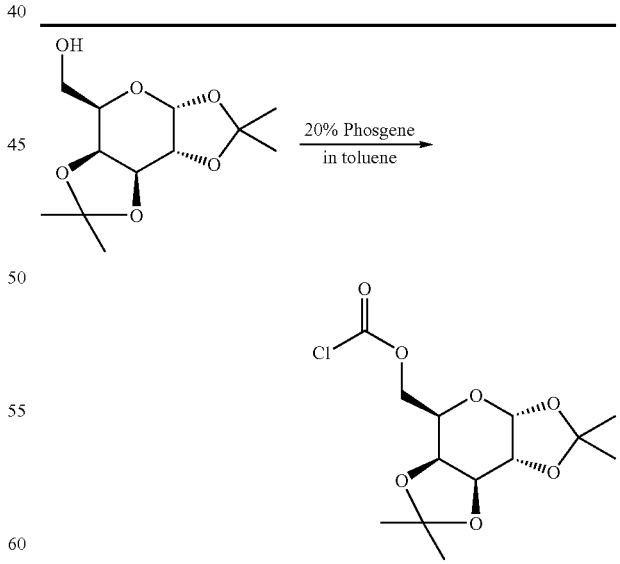

| Reagents | MW | Weight | mmoles | Molar Equivalents |
|---|---|---|---|---|
| 1,2:3,4-di-O-isopropylidene-D-galactopyranose | 260 | 1.00 g | 3.85 | 1 |
| 20% Phosgene in toluene | — | 20 ml | — | — |

9
Chloroformate of 1,2:3,4-di-O-isopropylidene-D-galactopyranose

To a stirring solution of 20% phosgene in toluene under an inert atmosphere was added 1,2:3,4-di-O-isopropylidene-D-galactopyranose via syringe. The resulting clear, colorless solution was stirred at ambient temperature for 30 minutes. After stirring, Ar(g) was bubbled through the solution for approximately 20 minutes to remove any excess phosgene.

10

Solvent was then removed and product dried under vacuum for 18 hours. Product was used without further purification or characterization.

Example 5

Preparation of Disaccharide-Hydrocodone

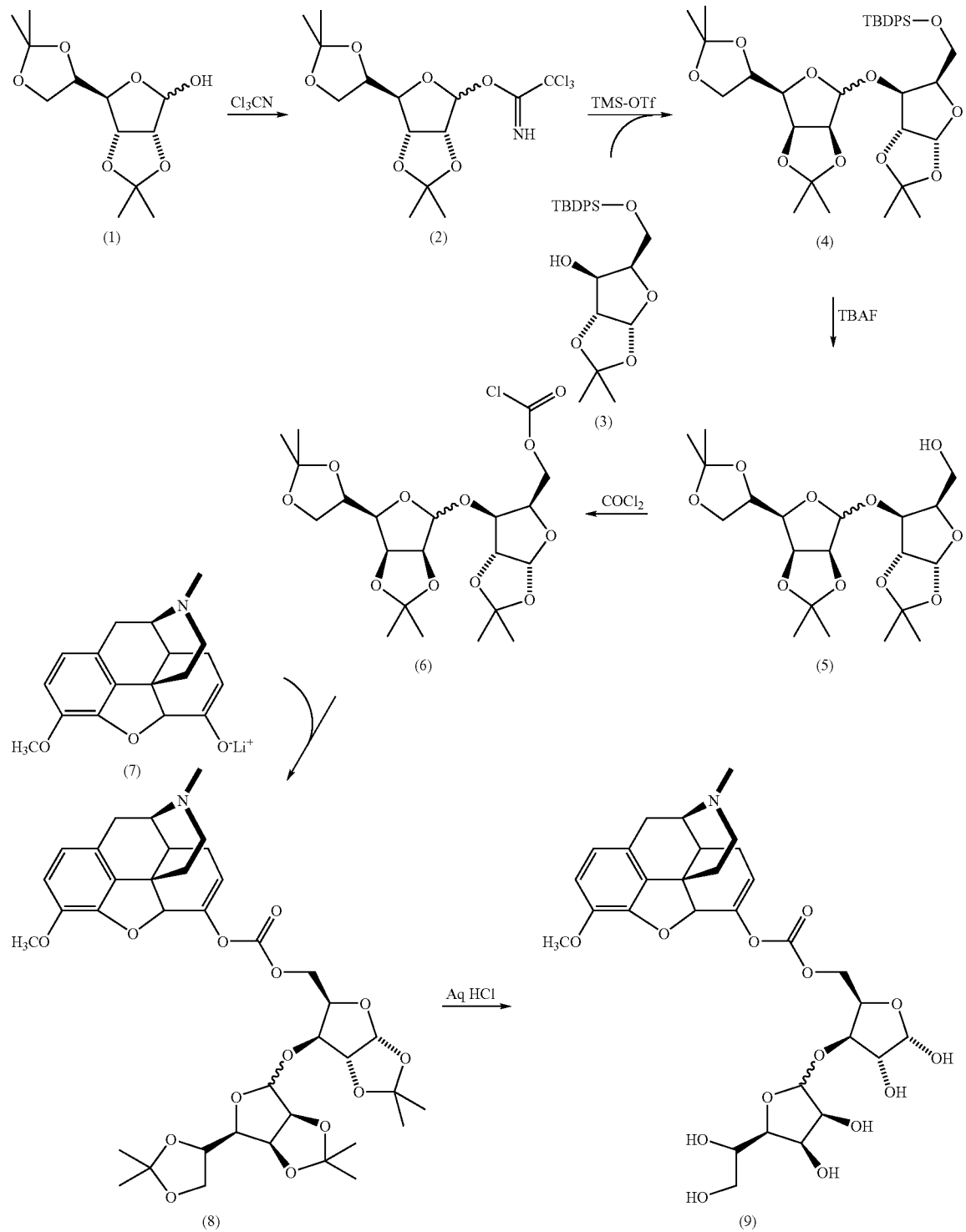

General Scheme for Preparation of Hydrocodone-Disaccharide Conjugates:

The protected mannofuranose (1) has been converted to the trichloroacetimidate (2) as described below. Based on literature precedent, this can in turn be coupled to an orthogonally-protected xylose (3), which affords the corresponding disaccharide (4). Disaccharide formation is promoted by the addition of a catalytic amount of acid. Use of an orthogonal protection scheme allows the selective removal of the silyl protecting group using tetrabutyl ammonium fluoride in the presence of the isopropylidene groups, affording the free primary alcohol (5). Employing methods already described in the preparation of galactose and ribose conjugates, this alcohol can then be converted to the chloroformate (6) and in turn coupled to the hydrocodone-enolate (7), resulting in the carbonate (8). Deprotection of (8) using standard protocols affords the hydrocodone-disaccharide conjugate (9)

Preparation of the Trichloroacetimidate of Mannofuranose (2):

Dissolved 2,3:5,6-Di-O-isopropylidene-D-mannofuranose (1, 0.50 g, 1.9 mmol) in 5 ml of anhydrous dichloromethane. Then, trichloroacetonitrile (0.67 ml, 6.7 mmol) was added to the solution followed by dry $K_2CO_3$ (0.54 g, 0 3.8 mmol). The reaction was then allowed to stir over night at room temperature under argon. Qualitative thin-layer chromatography (2:1 hexanes/acetone) of the reaction mixture indicated that the desired trichloroacetimidate had been formed, based on the disappearance of the spot corresponding to the mannofuranose starting material which correlated with the appearance of a new faster-running spot. This is consistent with literature precedence. The reaction was then filtered through fritted glass and the filtrate collected and freed of solvent by rotary-evaporation under high vacuum. This resulted in a viscous oil that solidified with storage over night under high vacuum.

Example 6

Stability of Narcotics in the "Kitchen Test"

To determine the accessibility of active narcotic from the synthetic conjugates, an attempt was made to release the narcotic from its conjugate. In a kitchen test, we determined the stability of the conjugates when subjected to conditions that would be available to any drug addict. Thus, the kitchen test is a model of "street-safeness" for the narcotics conjugates. The conjugates were heated in a water bath (80-90° C.) in a pH range (1-12) over a 1 hour time course. This pH range constitutes about any solution that can be found commercially at any grocery or drug store. The release of the narcotic from the conjugate was monitored by HPLC and quantified with a dose-response calibration curve of the parent narcotic.

Using only solutions that would be available to an addict, conjugates were dissolved in water. Water insoluble conjugates were either (a) dissolved in a minimum amount (≦5% v/v) of organic solvent [e.g., DMSO, methanol, or ethanol], (b) added as a suspension to the assay, or (c) dissolved completely in chloroform, and aliquoted to a test tube where the chloroform is evaporated, leaving only a known amount of conjugate. Upon preparation of the conjugate, the conjugate is added to the various pH solutions and heated for 0, 5, 15, or 60 minutes. At the indicated time point, each test tube was removed from the water bath and neutralized with a chilled phosphate buffer (100 mM, pH 7, 4° C.).

The kitchen test proceeds as follows:
1. pH solutions [1, 4, 7, 9, 12] prepared with HPLC grade $H_2O$ and titrated with NaOH or HCl
2. prepare hot water bath, keeping temperature at 80-90° C.
3. conjugates prepared at a concentration of 1 mg/ml as indicated above
4. 250 μl of conjugate added to 750 μl of pH solutions (final assay volume is 1 ml; if conjugate has been evaporated from $CHCl_3$, add 1 ml of pH solution to test tube)
5. immediately following the addition of conjugate to pH solution, place test tube in hot water bath (80-90° C.)
6. at indicated time point, remove test tubes from heat and neutralize with 1 ml of chilled phosphate buffer [0 time point is not heated, but immediately neutralized with phosphate buffer after the addition of conjugate to each pH solution]
7. before aliquoting each sample for HPLC analysis, the volume of each tube is adjusted to 2 ml to account for changes in concentration from evaporation Following HPLC analysis, the amount of released narcotic was extrapolated from a calibration curve of the parent drug and plotted as % narcotic released (w/w, based upon theoretical loading of conjugated species) vs. time.

Ribose-Hydrocodone conjugate TM34 was analyzed by the kitchen test. The results of the percent (relative to time zero) increase in free hydrocodone over time is presented in the following table.

| Kitchen Test Stability of Ribose-Hydrocodone | | | |
|---|---|---|---|
| | Minutes | | |
| | 5 | 15 | 60 |
| Solution | Percent Hydrocodone released* | | |
| pH 1 | 8 | 18 | 27.8 |
| pH 4 | 11 | 12.6 | 19.6 |
| pH 7 | 12 | 16 | 23.4 |
| pH 9 | 9 | 11 | 21 |
| pH 12 | 44 | 33 | 41.1 |

*Relative to zero hour level of free Hydrocodone

The Ribose conjugate is relatively stable at pHs other than pH 12, with the amount of hydrocodone released being 27.8% or less after one hour at 90° C. At pH 12 less than half the hydrocodone was released from the conjugate and no further release occurred after 5 minutes.

Example 7

Oral Bioavailability of Hydrocodone vs. Ribose-Hydrocodone

Doses of Hydrocodone Bitartarate and Ribose-Hydrocodone (TM34) containing equivalent amounts of hydrocodone (0.2143 mg) were administered in gelatin capsules to Male Srague-Dawley rats (approximately 300 g). The Hydrocodone content of Ribose-Hydrocodone conjugate was determined to be 66% by NMR.

TABLE 1

Oral Administration - Ribose-Hydrocodone vs. Hydrocodone-Bitartarate - Serum Levels (ng/ml)

| Hours | Ribose-HC #1 | Ribose-HC #2 | Ribose-HC #3 | Ribose-HC #4 | Hydrocodone #1 | Hydrocodone #2 | Hydrocodone #3 | Hydrocodone #4 |
|---|---|---|---|---|---|---|---|---|
| 0 | 0 | 0 | 0 | 0 | 0 | 0 | 0 | 0 |
| 0.5 | 12 | 7.3 | 12.9 | 12.3 | 10.2 | 14.8 | 6.3 | 8.6 |
| 1.5 | 8.4 | 11 | 8.7 | 10.6 | 6.8 | 7.9 | 10.1 | 4.7 |
| 3 | 2.4 | 7.6 | 2 | 1.6 | 0.6 | 8.3 | 3.5 | 0.2 |
| 5 | 1.3 | 2.6 | 0.2 | 0.5 | 4.6 | 0.7 | 2.7 | 0.1 |
| 8 | 1.1 | 2.9 | 0.8 | 1.2 | 2.1 | 2.1 | 0.9 | 5.5 |
| 12 | 1.2 | 2.2 | 0.7 | 0.9 | 0.5 | 1 | 0.9 | 2.6 |
| AUC | 33 | 54 | 29 | 33 | 37 | 47 | 35 | 37 |
| Ave. AUC +/− SD | | | 37 | 11 | Ave. AUC +/− SD | | 39 | 5 |

TABLE 2

Oral Administration - Mean Serum Levels (ng/ml +/− SD)

| | Ribose-HC | | Hydrocodone | |
|---|---|---|---|---|
| Hours | Ave. | SD | Ave. | SD |
| 0 | 0 | 0 | 0 | 0 |
| 0.5 | 11.1 | 2.6 | 10.0 | 3.6 |
| 1.5 | 9.7 | 1.3 | 7.4 | 2.3 |
| 3 | 3.4 | 2.8 | 3.2 | 3.7 |
| 5 | 1.2 | 1.1 | 2.0 | 2.0 |
| 8 | 1.5 | 0.9 | 2.7 | 2.0 |
| 12 | 1.3 | 0.7 | 1.3 | 0.9 |

TABLE 3

Oral Administration - Cmax (ng/ml) of Ribose-Hydrocodone vs. Hydrocodone

| Sample | Rat #1 | Rat #2 | Rat #3 | Rat #4 | Ave. | SD |
|---|---|---|---|---|---|---|
| Ribose-HC | 12 | 11 | 12.9 | 12.3 | 12.1 | 0.8 |
| Hydrocodone | 10.2 | 14.8 | 10.1 | 8.6 | 10.9 | 2.7 |

Bioavailability of Ribose-Hydrocodone TM34 was approximately equal to that of Hydrocodone-Bitaratarate when administered orally (Tables 1-3). The area under the curve (AUC) for Ribose-Hydrocodone was 95% of the AUC for Hydrocodone-Bitartarate (37 vs. 39, respectively). The mean peak serum concentration (Cmax) of Ribose-Hydrocodone was 111% of that of Hydrocodone-Bitratarate (12.1 vs. 10.9, respectively). The serum concentration curves of Ribose-Hydrocodone TM34 vs. Hydrocodone-Bitartarate administered orally are shown in FIG. 1.

Example 8

Intranasal Bioavailability of Hydrocodone vs. Ribose Hydrocodone

Doses of Hydrocodone Bitartarate and Ribose-Hydrocodone (TM34) containing equivalent amounts of Hydrocodone (0.2143 mg) were administered intranasally to Male Srague-Dawley rats (approximately 300 g). Doses were administered in phosphate buffered saline directly into the nasal flares of the rats.

Figure 2:
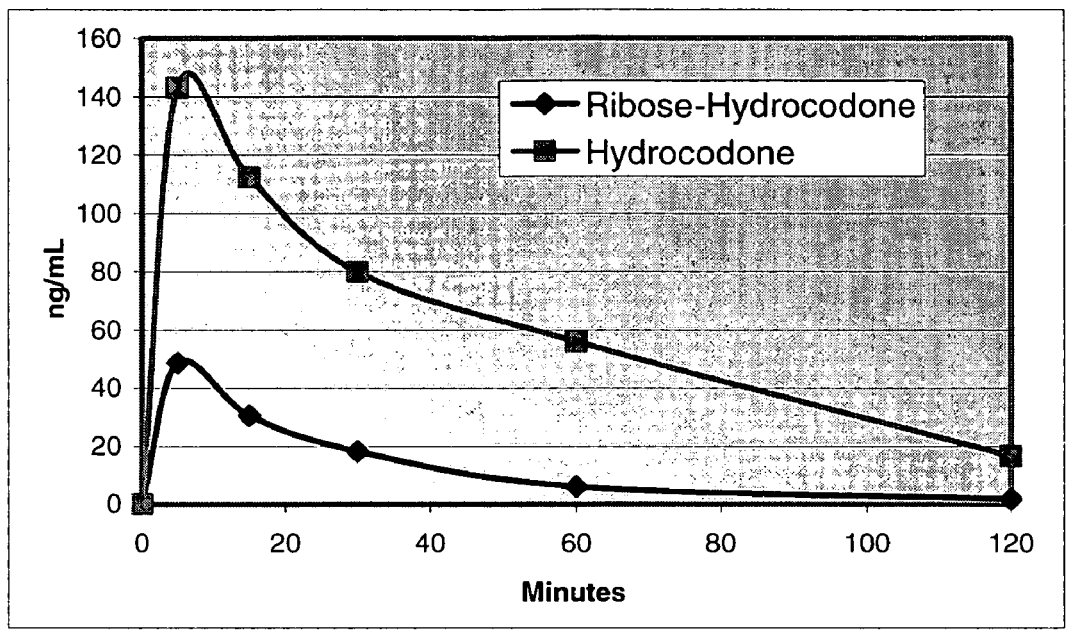
FIG. 2. illustrates mean hydrocodone serum levels compared to a ribose-hydrocodone conjugate intranasally delivered.

Bioavailability of Ribose-Hydrocodone TM34 was decreased when administered intranasally as compared to that of Hydrocodone-Bitartarate administered by the same route. The AUC of Ribose-Hydrocodone was 20% of the AUC of Hydrocodone (1,490 vs. 7,303, respectively). Further, Cmax of Ribose-Hydrocodone was 36% of the AUC of Hydrocodone (51 vs. 143, respectively). The serum concentration curves of Ribose-Hydrocodone TM34 vs. Hydrocodone-Bitartarate administered intranasally are shown in FIG. 2.

Example 9

Intravenous Bioavailability of Hydrocodone vs. Ribose Hydrocodone

Doses of Hydrocodone Bitartarate and Ribose-Hydrocodone (TM34) containing equivalent amounts of Hydrocodone (0.2143 mg) were administered intravenously to Male Srague-Dawley rats (approximately 300 g). Doses were administered by tail vein injection in phosphate buffered saline.

Figure 3:
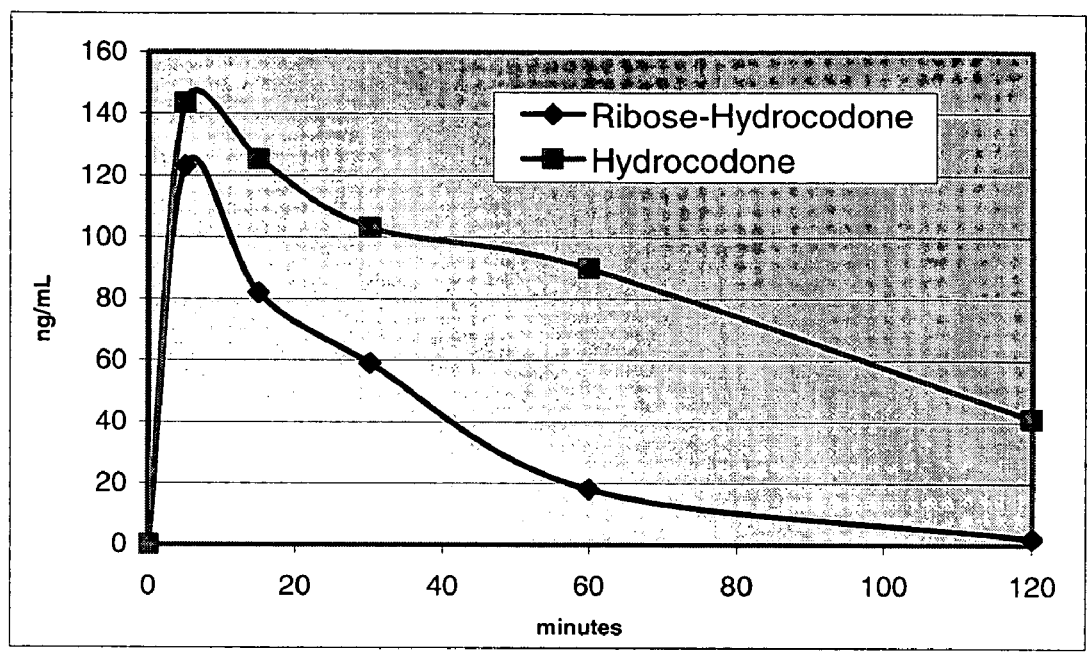
FIG. 3. illustrates mean hydrocodone serum levels compared to a ribose-hydrocodone conjugate intravenously delivered.

Bioavailability of Ribose-Hydrocodone TM34 was decreased when administered intravenously as compared to that of Hydrocodone-Bitartarate administered by the same route. The AUC of Ribose-Hydrocodone was 41% of the AUC of Hydrocodone (4,145 vs. 10,233, respectively). Cmax of Ribose-Hydrocodone was 86% of the AUC of Hydrocodone (123 vs. 143, respectively), thus decreased bioavailability was substantially the result of an increased clearance rate for Ribose-Hydrocodone. The serum concentration curves of Ribose-Hydrocodone TM34 vs. Hydrocodone-Bitartarate administered intravenously are shown in FIG. 3.

Collectively, examples 7 through 9 illustrate that attachment of a ribofuranose moiety to the C6 position of Hydrocodone affords a compound with decreased potential for abuse. Oral bioavailability of this compound is maintained, whereas intranasal and intravenous bioavailability are substantially decreased thereby diminishing the euphoric effect of the compound when administered by these routes. Further, example 8 illustrates that absorption of the Ribose-Hydrocodone conjugate through the intranasal membrane is substantially blocked indicating that the ability to permeate cell membranes, likely including the blood brain barrier, is diminished. This property may further decrease the potential for abuse by either intranasal or intravenous administration of narcotic conjugates since the narcotic must permeate the blood brain barrier to elicit euphoria. Example 9 illustrates an increased clearance rate for intravenously administered Ribose-Hydrocodone conjugate, providing an additional mechanism for decreased potential abuse of narcotic conjugates.

Example 10

Oral Bioavailability of Hydrocodone vs. Galactose-Hydrocodone

Doses of Hydrocodone Bitartarate and Galactose-Hydrocodone (TMb20) containing equivalent amounts of hydrocodone (0.2143 mg) were administered in gelatin capsules to Male Srague-Dawley rats (approximately 300 g).

Figure 4:
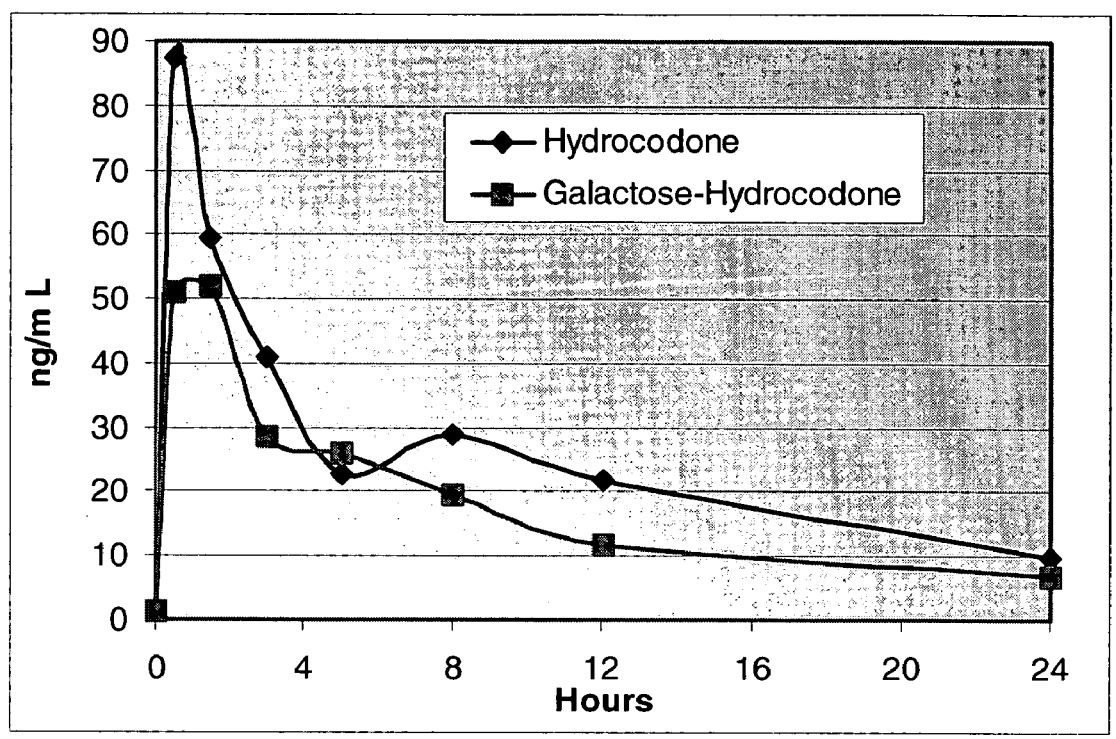
FIG. 4. illustrates mean hydrocodone serum levels compared to a galactose-hydrocodone conjugate orally delivered.

Bioavailability of Galactose-Hydrocodone (TMb20) approached that of Hydrocodone-Bitaratarate when administered orally. The area under the curve (AUC) for Galactose-Hydrocodone was 70% of the AUC for Hydrocodone-Bitartarate (422 vs. 601, respectively). The mean peak serum concentration (Cmax) of Galactose-Hydrocodone was 72% of that of Hydrocodone-Bitratarate (61 vs. 85, respectively). The serum concentration curves of Galactose-Hydrocodone (TMb20) vs. Hydrocodone-Bitartarate administered orally are shown in FIG. 4.

Example 11

Intranasal Bioavailability of Hydrocodone vs. Galactose Hydrocodone

Doses of Hydrocodone Bitartarate and Galactbose-Hydrocodone (TM34) containing equivalent amounts of Hydrocodone (0.2143 mg) were administered intranasally to Male Srague-Dawley rats (approximately 300 g). Doses were administered in phosphate buffered saline directly into the nasal flares of the rats.

Figure 5:
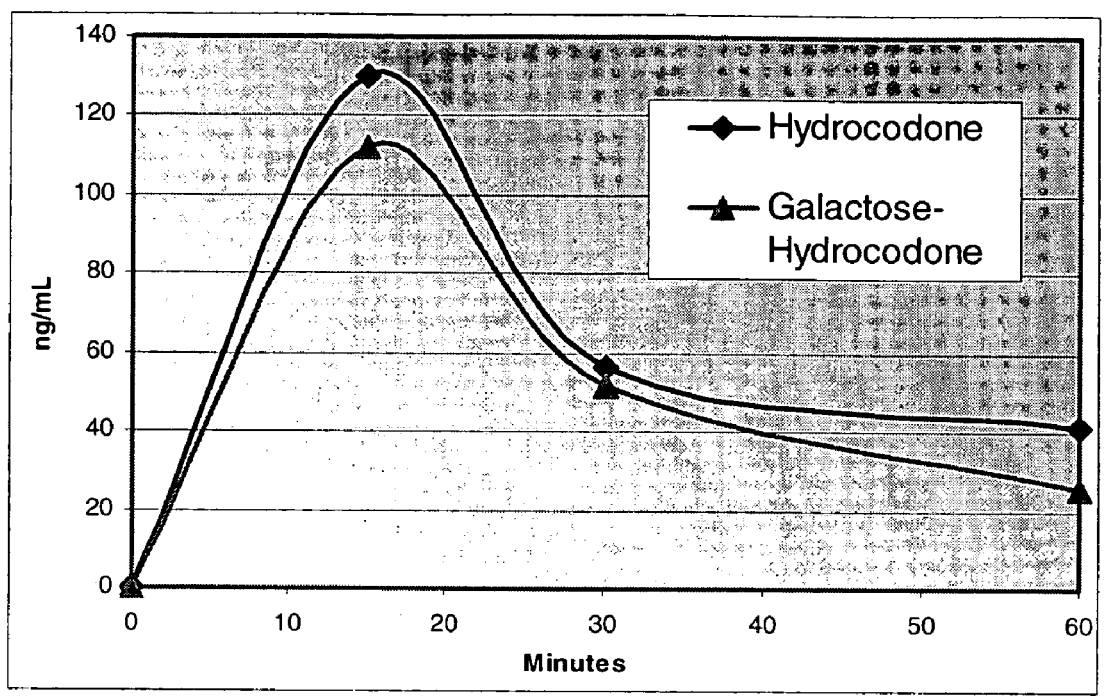
FIG. 5. illustrates mean hydrocodone serum levels compared to a galactose-hydrocodone conjugate intranasally delivered.

Bioavailability of Galactose-Hydrocodone TMb20 was marginally decreased when administered intranasally as compared to that of Hydrocodone-Bitartarate administered by the same route. The AUC of Galactose-Hydrocodone was 83% of the AUC of Hydrocodone (3,203 vs. 3,845, respectively). Further, Cmax of Galactose-Hydrocodone was 36% of the AUC of Hydrocodone (130 vs. 112, respectively). The serum concentration curves of Galactose-Hydrocodone TM34 vs. Hydrocodone-Bitartarate administered intranasally are shown in FIG. 5.

What is claimed is:

1. An oral pharmaceutical composition comprising:
   hydrocodone; and
   a disaccharide covalently bound to the hydrocodone via an ester or carbonate bond through a hydroxyl group of the disaccharide and an oxygen atom in the hydrocodone in a manner that renders the hydrocodone pharmacologically inactive or substantially diminishes its activity until unbound hydrocodone is released.

2. An oral pharmaceutical composition comprising a disaccharide covalently bound to hydrocodone via an ester or carbonate group through a hydroxyl group of the disaccharide and an oxygen atom in the hydrocodone in a manner that renders the hydrocodone pharmacologically inactive or substantially diminishes its activity until the unbound hydrocodone is released, wherein the hydrocodone covalently bound to the carbohydrate has the formula:

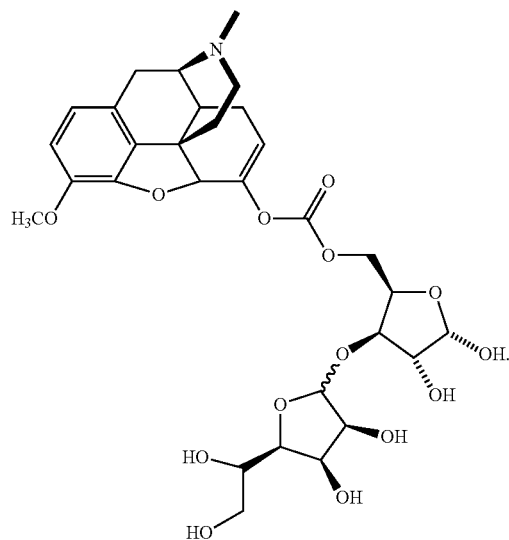

(9)

3. A compound of the formula:

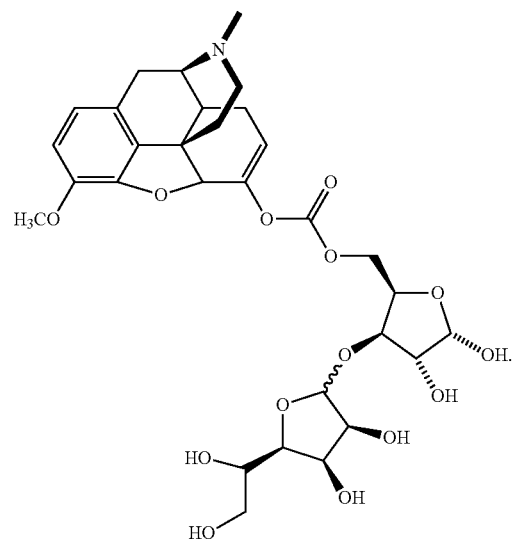

(9)

* * * * *